US009872931B2

(12) United States Patent
Andersson et al.

(10) Patent No.: US 9,872,931 B2
(45) Date of Patent: Jan. 23, 2018

(54) REMOVABLE STERILIZATION RACK AND STERILIZATION APPARATUS

(75) Inventors: Jonas Andersson, Halmstad (SE); Ola Kristiansson, Gullbrandstorp (SE); Henrik Einarsson, Fjaras (SE)

(73) Assignee: GETINGE STERILIZATION AB, Getinge (SE)

( * ) Notice: Subject to any disclaimer, the term of this patent is extended or adjusted under 35 U.S.C. 154(b) by 413 days.

(21) Appl. No.: 14/404,767

(22) PCT Filed: Jun. 14, 2012

(86) PCT No.: PCT/EP2012/061378
§ 371 (c)(1),
(2), (4) Date: Jan. 19, 2015

(87) PCT Pub. No.: WO2013/185831
PCT Pub. Date: Dec. 19, 2013

(65) Prior Publication Data
US 2015/0147232 A1    May 28, 2015

(51) Int. Cl.
*A61L 2/26*    (2006.01)
*A61L 2/07*    (2006.01)
(Continued)

(52) U.S. Cl.
CPC .................. *A61L 2/26* (2013.01); *A61L 2/04* (2013.01); *A61L 2/07* (2013.01); *A61L 2/18* (2013.01); *A61L 2202/15* (2013.01)

(58) Field of Classification Search
CPC ..... A61L 2/04; A61L 2/07; A61L 2/18; A61L 2/24; A61L 2/26; A61L 2202/122;
(Continued)

(56) References Cited

U.S. PATENT DOCUMENTS 3,511,252 A     5/1970  Kennedy et al.
2003/0127113 A1*  7/2003  Lavoie ................ A61L 2/18
                                                134/25.2
(Continued)

FOREIGN PATENT DOCUMENTS

JP        S507040 U    1/1975
WO    WO-2009/016111 A1   2/2009

OTHER PUBLICATIONS

International Search Report PCT/ISA/210 for International Application No. PCT/EP2012/061378 dated Feb. 11,2013.
(Continued)

*Primary Examiner* — Timothy Cleveland (57) ABSTRACT

A removable sterilization rack for supporting objects to be sterilized inside a sterilization apparatus is disclosed. The sterilization rack includes a support structure for supporting the objections; at least one opening for directing a flow of a fluid towards the objects when the objects are supported by the support structure; a docking port for docking with a fluid supply port in the sterilization apparatus and for receiving the fluid from the fluid supply port of the sterilization apparatus; and a conduit arranged and configured to bring the docking port in fluid connection with the at least one opening. The sterilization rack further includes a marker configured to provide a contactless positioning indication to the sterilization apparatus when the docking port is in a position to receive the fluid from the fluid supply port of the sterilization apparatus.

8 Claims, 6 Drawing Sheets

(51) Int. Cl.
*A61L 2/04* (2006.01)
*A61L 2/18* (2006.01)

(58) Field of Classification Search
CPC ........... A61L 2202/123; A61L 2202/15; A61L 2202/23; A61L 2202/24
See application file for complete search history.

(56) References Cited

U.S. PATENT DOCUMENTS

2008/0005923 A1 1/2008 Zwingenberger et al.
2009/0311135 A1 12/2009 Zwingenberger et al.
2010/0170544 A1 7/2010 Casonato

OTHER PUBLICATIONS

Written Opinion of the International Searching Authority PCT/ISA/237 for International Application No. PCT/EP2012/061378 dated Feb. 11, 2013.

* cited by examiner

REMOVABLE STERILIZATION RACK AND STERILIZATION APPARATUS

TECHNICAL FIELD OF THE INVENTION

The present invention relates to a removable sterilization rack and to a sterilization apparatus for sterilization of objects by means of a sterilization fluid, such as e.g. steam.

BACKGROUND OF THE INVENTION

A common technique to sterilize objects used in e.g. hospitals, laboratories and the pharmaceutical industry is to use a sterilization apparatus such as an autoclave. A sterilization apparatus typically comprises a chamber for receiving the objects to be sterilized and a fluid system for supplying a sterilization medium to the objects inside the chamber. The sterilization medium may for example be supplied to the objects by nozzles.

In steam sterilization, steam is introduced into the chamber and the temperature is increased to a sterilization temperature. After a predefined sterilization time, which depends on the sterilization temperature used, the steam is evacuated from the chamber.

The total process time, which is often of great importance to the user of the sterilization apparatus, mainly consists of the above-mentioned sterilization time, the time for introducing steam and achieving the sterilization temperature, and the time for evacuating the chamber. For certain kinds of objects to be sterilized, additional processing time before or after the actual sterilization may be required to further process the objects. For example, closures that are sterilized in bags may be subjected to drying cycles to remove steam condensate in the bags. A further example is the sterilization of bottles with content, which may require additional cooling time due to their relatively large thermal mass.

Any such additional processing adds to the total process time during which the objects occupy the sterilization apparatus.

It would be desirable to provide for a reduction of the total process time of the sterilization process.

SUMMARY

An object of the invention is to overcome the above problems, and to provide a removable sterilization rack and a sterilization apparatus which provide for a reduction of the total process time of the sterilization process.

This and other objects, which will become apparent in the following, are accomplished by means of removable sterilization rack and a sterilization apparatus defined in the accompanying claims.

According to a first aspect of the invention, a removable sterilization rack for supporting objects to be sterilized inside a sterilization apparatus is provided. The removable sterilization rack comprises:

a support structure for supporting the objects;

at least one opening for directing a flow of a fluid towards the objects when the objects are supported by the support structure;

a docking port for docking with a fluid supply port comprised in the sterilization apparatus and receiving the fluid from the fluid supply port of the sterilization apparatus; and a conduit arranged and configured to bring the docking port in fluid flow connection with the at least one opening, wherein the sterilization rack comprises a marker configured to provide a contactless positioning indication to the sterilization apparatus when the docking port is in a position to receive the fluid from the fluid supply port of the sterilization apparatus.

The present invention is based on the realization that by providing a removable sterilization rack which may receive a fluid from the sterilization apparatus and furthermore, direct the flow of fluid through an opening in the rack towards the objects to be sterilized, the total process time may be reduced. By providing at least one opening in the rack, fluid may be directed towards the objects more efficiently compared to if the opening would have been located in a wall of the chamber, and hence the process may be carried out in a more efficient manner. For example, if the fluid is air and the process to be carried out is drying, the time for the objects to be dried may be reduced since the fluid may be directed towards the objects implying an increased heat transfer from the objects. The present invention is further based on the realization that by providing the removable sterilization rack with a marker for contactless positioning indication, the docking port comprised in the sterilization rack may be connected to the fluid supply port comprised in the sterilization apparatus in a controllable and reliable manner. Thus, the fluid supply port may supply fluid to the docking port, through the sterilization rack and further, via at least one opening in the rack, to the objects to be sterilized.

The at least one opening may be directed along and/or perpendicular to the support structure. The at least one opening may also be directed with an angle to the support structure. Furthermore, the removable sterilization rack may comprise a plurality of openings located at various positions of the sterilization rack. The positioning of the openings may be arranged such that a directed flow of fluid is provided through the sterilization apparatus. For example, openings close to a chamber inlet of the sterilization apparatus for inserting objects and/or the sterilization rack may be directed away from the chamber inlet such that a flow of fluid is provided away from the chamber inlet.

The fluid which flows from the sterilization apparatus to the at least one opening in the sterilization rack may be air, such as hot air or cold air, water, steam or a combination of the four. Thus, is should be understood that the objects to be sterilized may be subject to other process steps, such as heating, drying or cooling. Hot air may for example be used if the objects supported by the sterilization rack are to be heated or dried. Cold air may be used if the objects supported by the sterilization rack are to be cooled. Steam may be used if the objects supported by the sterilization rack are to be sterilized. The use of other fluids is also conceivable within the scope of the invention. For example, another sterilization medium than steam, such as e.g. formalin and/or formaldehyde or superheated water, may be provided by the sterilization rack and used in the sterilization process.

It is possible to use a conventional passage for supplying the sterilization medium, such as steam, formalin, formaldehyde and/or superheated water, to the sterilization apparatus for sterilizing objects, while the openings in the removable sterilization rack may be arranged to e.g. supply hot air for drying the objects and/or cold air or water for cooling the objects. Of course, the use of any combination of different fluids, either using a conventional passage in the sterilization apparatus and/or the openings in the sterilization rack is within the scope of the invention.

By having a removable sterilization rack, the rack may be loaded with objects to be sterilized prior to the insertion of the sterilization rack into the sterilization apparatus. Hereby, the handling of the objects to be sterilized/heated/dried/cooled are facilitated. Furthermore, different sterilization racks may be optimized for different kinds of objects. For example, one sterilization rack may be arranged to be used for objects to be heated or dried by the fluid supplied by the at least one opening in the sterilization rack, while another sterilization rack may be arranged to be used for objects to be sterilized by the fluid supplied by the at least one opening in the sterilization rack. In a further example, one type of sterilization racks may be arranged to be used for objects to be cooled by the fluid supplied by the at least one opening in the sterilization rack. An operator may choose between several predefined sterilization process programs, which are tailored to get an optimized result, depending on the objects' design and nature, by having different ways of heating, sterilizing, drying and/or cooling.

Accordingly, various embodiments of the present invention provide removable sterilization racks which are able to receive and transport a fluid from the sterilization apparatus to the objects to be sterilized. Furthermore, various embodiments of the present invention provide a marker for contactless position indication to the sterilization apparatus.

According to at least one embodiment of the removable sterilization rack of the present invention, the marker may comprise a magnet. Hence, the sterilization apparatus may advantageously be provided with a sensor, such as e.g. a hail sensor, for sensing the magnet. Hereby, an easy and cheap contactless indication position of the removable sterilization rack may be achieved. According to at least one embodiment of the present invention, the marker may comprise an inductive device. Thus it is possible to detect if the docking port is connected to the fluid supply port without the need of holes or apertures extending through the fluid supply port.

In embodiments of the present invention, the marker may be comprised in the docking port. Such a placement of the marker may facilitate the positioning indication of the docking port to the supply port comprised in the sterilization apparatus. Correspondingly, the fluid supply port may comprise the sensor for detecting the marker.

In order to supply the fluid from the sterilization apparatus to the objects via the removable sterilization rack, the removable sterilization rack comprises means for being in fluid flow connection with the sterilization apparatus. According to the first aspect of the invention this is performed by the docking port which is to be connected to the fluid supply port comprised in the sterilization apparatus, and a conduit arranged and configured to bring the docking port in fluid flow connection with the at least one opening in the sterilization rack. Hereby, the fluid may flow from the sterilization apparatus to the objects via at least one opening in the sterilization rack. At least a portion of the conduit between the support structure and the docking port may be flexibly arranged in order for the docking port to more easily connect to the fluid supply port. Moreover, the removable sterilization rack may further comprise a conduit support arranged to support and retain the conduit within its flexible limits in order for the conduit not to break or be permanently deformed through rough handling.

Furthermore, in order to supply the fluid via the sterilization rack, the support structure according to various embodiments of the invention may comprise a tubular frame, which tubular frame constitutes at least a part of the conduit. Hence, the tubular frame may be in fluid flow connection with the sterilization apparatus and the at least one opening. According to at least one embodiment of the present invention, the conduit is a continuation of the tubular frame. According to yet another embodiment of the invention, the conduit may be connected to the docking port.

The tubular frame may comprise at least one opening for directing a flow of a fluid towards the objects when the objects are supported by the support structure. According to at least one example embodiment of the invention, the support structure supporting the objects to be sterilized may comprise the tubular frame, which tubular frame constitutes at least a part of the conduit and comprises at least one opening. In this manner, the support structure both supports the objects to be sterilized and comprises means for supplying the flow of fluid to the objects. Thus, the fluid may be directed towards the objects to be sterilized, thereby providing for a further reduction of the total process time.

In embodiments of the present invention, the support structure may further comprise a shelf having a tubular portion, which tubular portion is in fluid flow connection with the tubular frame and has at least one opening for directing a flow of a fluid towards the objects when the objects are supported by the support structure. Such a positioning of the at least one opening may allow for an improved direction of the fluid towards the objects to be sterilized.

According to at least one example embodiment of the invention, each of the tubular frame and the tubular portion of the shelf may comprise at least one opening for directing a flow of fluid towards the objects to be sterilized.

According to further embodiments, the shelf may be releasably attached to the tubular frame using at least one fastener configured to mechanically attach the tubular portion of the shelf to the tubular frame and to provide a flow channel between the tubular frame and the tubular portion of the shelf. In this way, different shelves may be attached to the tubular frame. For example, the different shelves may be used for different objects. For example, one type of shelf may be used for objects to be heated or dried by the fluid supplied by the at least one opening in the sterilization rack, while another type of shelf may be used for objects to be sterilized by the fluid supplied by the at least one opening in the sterilization rack. In a further example, one type of shelves may be used for objects to be cooled by the fluid supplied by the at least one opening in the sterilization rack.

Moreover, by using a fastener configured to mechanically attach the tubular portion of the shelf to the tubular frame and to provide a flow channel between the tubular frame and the tubular portion of the shelf, the function of the fastener is a combination of attaching the shelf to the tubular frame while providing a fluid flow connection between the same. Hereby, there is no need for using one component for fastening the shelf to the tubular frame and another component for transporting the fluid from the tubular frame to the shelf.

The fastener may comprise a hollow screw to provide a flow channel between the tubular frame and the tubular portion of the shelf.

According to a second aspect of the present invention, a sterilization apparatus, for sterilization of objects to be sterilized, is provided. The sterilization apparatus comprises: a sterilization chamber configured to receive the removable sterilization rack according to the first aspect of the invention; an inlet for admission of a sterilization medium into the sterilization chamber; an outlet for controllable evacuation of the sterilization medium from the sterilization chamber; a fluid supply port comprising a connecting device and a controllable fluid outlet; a sensor arranged and configured to provide a positioning signal indicative of a presence of the marker comprised in the sterilization rack according to the first aspect of the invention when the docking port of the sterilization rack according to the first aspect of the invention is in a position to receive fluid from the fluid supply port; and a control unit connected to the sensor and the connecting device and configured to control the connecting device to bring the outlet of the fluid supply port in fluid flow connection with the docking port comprised in the sterilization rack according to the first aspect of the invention in response to the positioning signal from the sensor.

Effects and features of this second aspect of the present invention are largely analogous to those described above in connection with the first aspect of the invention.

The fluid supply port may be configured to supply any kind of fluid from the sterilization apparatus to the removable sterilization rack. For example, the fluid supply port may supply air, such as hot air for heating and/or drying the objects to be sterilized, cold air or water for cooling the objects to be sterilized, or a sterilization medium, such as e.g. steam, superheated water, formalin or formaldehyde, to sterilize the objects.

The sterilization chamber may comprise a chamber fluid inlet providing the sterilization medium directly to the chamber and not via the sterilization rack. Hereby, the chamber fluid inlet may provide for the sterilization medium, such as e.g. steam, superheated water, formalin or formaldehyde while the removable sterilization rack provides openings for directing a fluid to the objects for heating, drying and/or cooling.

According to at least one example embodiment of the invention, the connecting device may comprise an inflatable seal. Hereby, a cheap and reliable seal is achieved. The inflatable seal may be circumferentially positioned at a certain radial distance from the fluid outlet of the fluid supply port. Hereby, the fluid supply port and the docking port of the sterilization rack may be in fluid flow connection without being perfectly adjusted relative each other and sealed by the inflatable seal.

According to one example embodiment of the invention, the sensor is configured to detect a magnet. Hereby, the sensor detects the marker in the sterilization rack when the marker comprises the magnet. Thus a cheap and reliable detecting system may be achieved.

Furthermore, the sensor may be arranged outside the sterilization chamber and be separated from an interior of the sterilization chamber by a chamber wall.

According to one embodiment of the invention, the fluid supply port may comprise a fluid supply conduit and a fluid supply outlet, wherein the fluid supply conduit leads to the fluid supply outlet. The fluid supply conduit may be arranged to supply a fluid flow to the fluid supply outlet. Furthermore, the fluid supply port may comprise a drain pipe for draining the removable sterilization rack.

According to one embodiment of the invention, the fluid supply port may further comprise a valve arranged along said fluid supply conduit, the valve being arranged to close and open the fluid supply conduit to the fluid supply outlet, and wherein the drain pipe may be arranged such that a fluid path is provided between the fluid supply conduit and the drain pipe when the valve is arranged to close the fluid supply conduit from the fluid supply outlet. Hereby microbiological growth in fluid supply conduit and the drain pipe may be removed by e.g. steam, so called "steam-in-place".

BRIEF DESCRIPTION OF THE DRAWINGS

These and other aspects of the present invention will now be described in more detail, with reference to the appended drawings showing example embodiments of the invention, wherein:

FIG. 1b is an enlargement of the connection between the removable sterilization rack and the sterilization apparatus in FIG. 1a;

FIG. 2b is an enlargement of the connection between the shelves and the frame in FIG. 2a;

DETAILED DESCRIPTION OF AN EXAMPLE EMBODIMENT OF THE INVENTION

In the following description, the present invention is mainly described with reference to a sterilization apparatus for sterilizing of objects and a removable sterilization rack configured to be arranged inside a sterilization apparatus. Furthermore, the invention is described with reference to the connection between the sterilization apparatus and the removable sterilization rack.

It should, however, be noted that this description by no means limits the scope of the invention, which is equally applicable to, for example, sterilization apparatus and removable sterilization racks with other configurations using the same type of connection connecting the sterilizing apparatus to the removable sterilization rack.

Figure 1A:
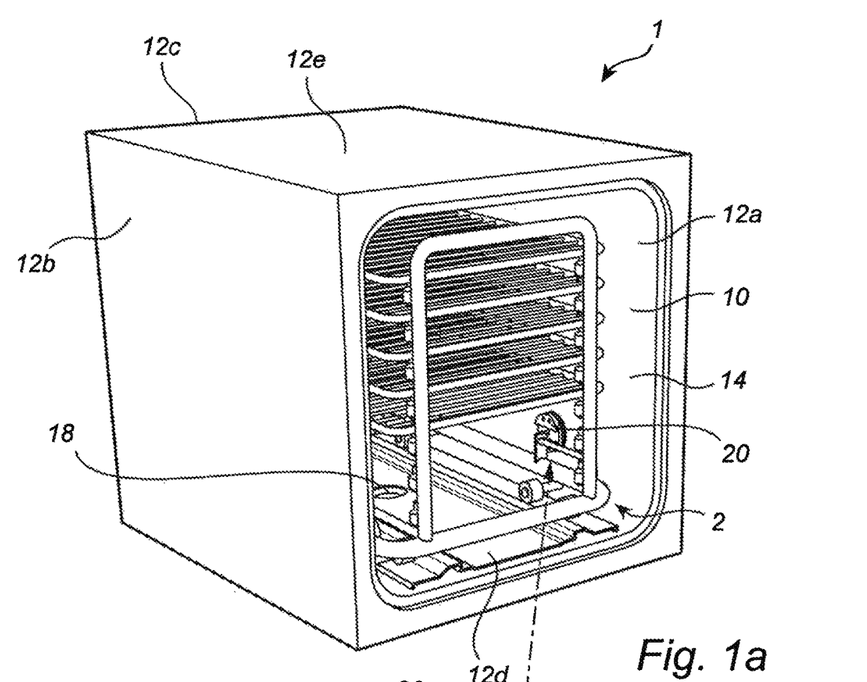
FIG. 1a illustrates a sterilization apparatus and a removable sterilization rack according to at least one example embodiment of the present invention.

FIG. 1a illustrates an exemplary sterilization apparatus 1 and a removable sterilization rack 2 arranged inside the sterilization apparatus 1. The sterilization apparatus 1 comprises a chamber 10 having three walls 12a, 12b, 12c, a floor 12d and a ceiling 12e. A chamber inlet 14 for inserting objects and/or the removable sterilization rack 2 is arranged opposite the wall 12c. A door (not shown) may be arranged to seal the chamber inlet 14. The chamber 2 may be provided with two chamber inlets 14 for inserting objects and/or the removable sterilization rack 2 arranged such that the chamber inlets 14 are opposite each other. In the floor 12d, a drain 18 is arranged for draining the chamber. Furthermore, a fluid supply port 20 is arranged in one of the walls 12a of the chamber 1. Additionally, passages/openings (not shown) for supplying fluid to the chamber may be provided in the walls 12a, 12b, 12c, the floor 12d and/or the ceiling 12e.

Figure 1B:
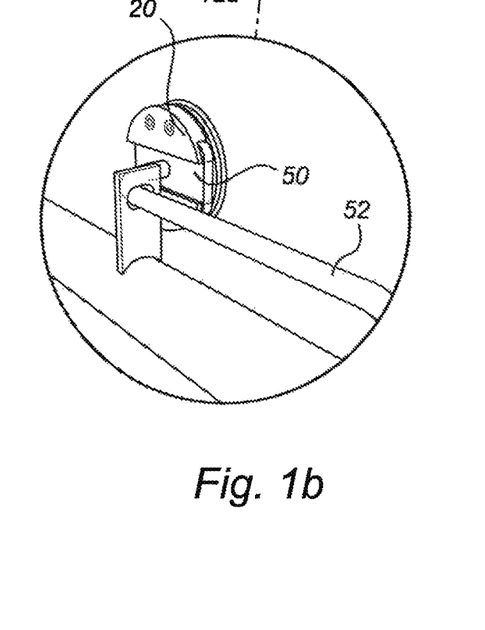

With reference to FIG. 1b, which is an enlarged view of the connection between the sterilization rack 2 and the sterilization apparatus 1, a docking port 50 comprised in the sterilization rack 2 is connected to a conduit 52 comprised in the sterilization rack 2. The docking port 50 is connected to the fluid supply port 20 such that the sterilization apparatus 1 may be in fluid flow contact with the sterilization rack 2. The connection between the docking port 50 and the fluid supply port 20 is further described in FIG. 3 and FIG. 4.

Figure 2A:
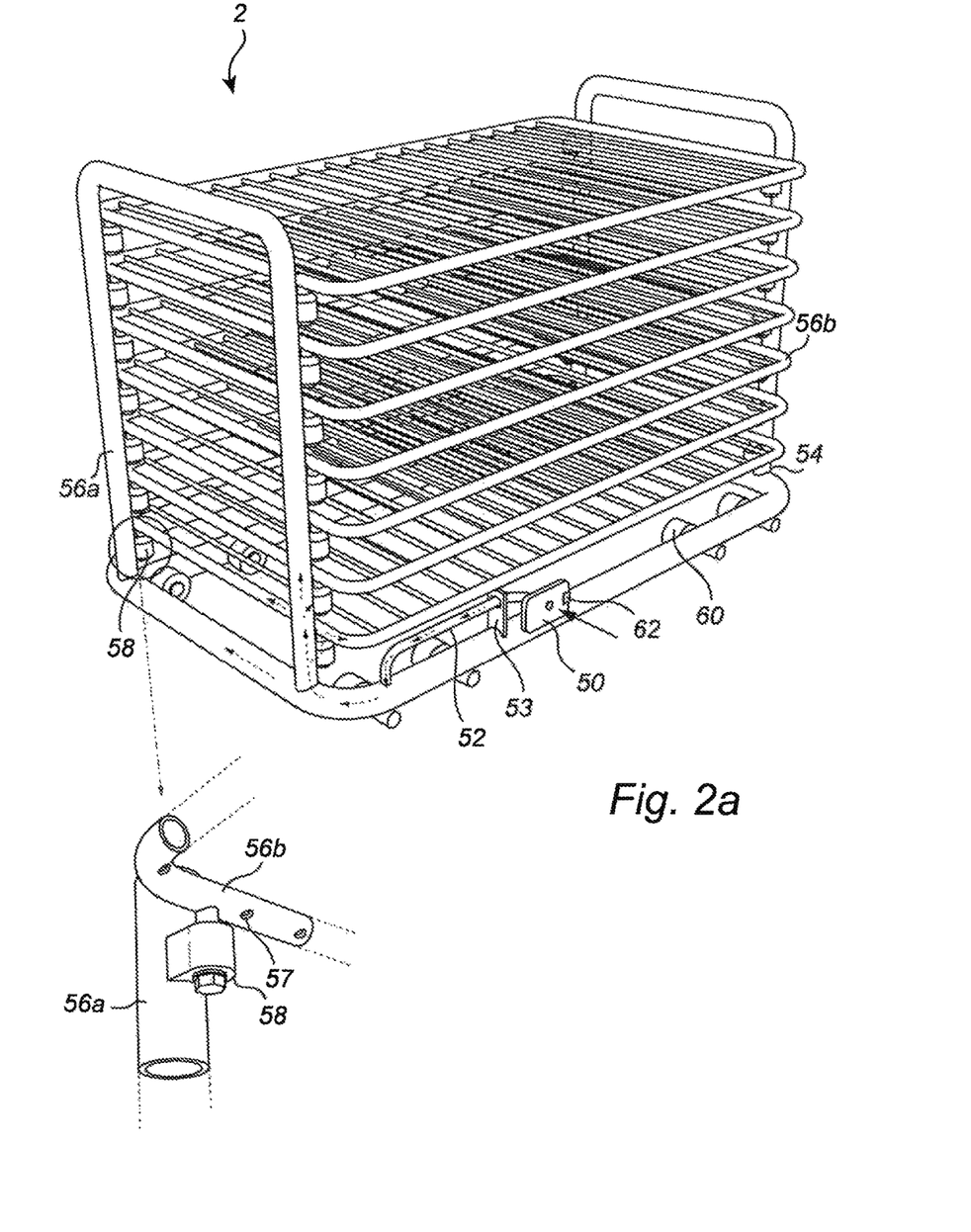
FIG. 2a illustrates a removable sterilization rack according to at least one example embodiment of the present invention.

The removable sterilization rack 2 will now be described in greater detail with reference to FIG. 2a. As is illustrated in FIG. 2a, the sterilization rack 2 comprises a support structure 54 for supporting objects (not shown), the docking port 50 previously described with reference to FIG. 1b for connecting to the fluid supply port 20 of the sterilization apparatus 1, and the conduit 52 previously described with reference to FIG. 1b connected to the support structure 54, a conduit support 53 arranged on the frame 56a for guiding the conduit 52 between the docking port 50 and the support structure 54, and the docking port 50. The support structure 54 comprises a frame 56a and shelves 56b connected to the frame 56a by means of connectors 58. In FIG. 2a, seven shelves 56b are attached to the frame 56a. The number of shelves 56b does not limit the scope of the invention as any number of shelves 56b may be attached to the frame 56a. Furthermore, the frame 56a is provided with wheels 60, of which six are seen in FIG. 2a, for facilitating the transportation of the sterilization rack 2 into and out of the chamber 10 of sterilization apparatus 1.

The docking port 50 further comprises a marker 62, here in the form of a magnet 62 for contactless positioning indication of the sterilization rack 2 when the sterilization rack 2 is arranged inside the sterilization apparatus 1.

Prior to the insertion of the sterilization rack 2 into the chamber 10 of the sterilization apparatus 1, objects (not shown) are loaded on the supporting structure 54, for example on at least one of the shelves 56b. The insertion of the sterilization rack 2 into the chamber 10 is facilitated by the wheels 60. During the insertion of the sterilization rack 2 into the chamber 10, the docking port 50 is arranged to be connected to the fluid supply port 20 of the sterilization apparatus 1. The conduit 52 is flexibly attached to the frame 56a in order to facilitate the connection of the docking port 50 to the fluid supply port 20. Moreover, the conduit 52 is able to move within limits restrained by the conduit support 53, in order for the conduit 52 not to be bent beyond its flexible limits.

Furthermore, as illustrated in FIG. 2a, the conduit 52, the frame 56a, the shelves 56b and the connectors 58 are tubular, allowing fluid to pass through the sterilization rack 2. Owing to this, when the sterilization rack 2 is in fluid flow connection to the sterilization apparatus 1, fluid may be distributed from the sterilization apparatus 1 via the docking port 50 and the conduit 52 to the support structure 54 as indicated by arrows in FIG. 2a.

FIG. 2a also illustrates an enlarged view of one of the connectors 58, connecting the shelves 56b to the frame 56a. The shelf 56b in the enlarged view in FIG. 2a further comprises openings 57 for directing the flow of fluid distributed through the support structure 54 towards the objects (not shown). In the embodiment illustrated in FIG. 2a, openings 57 are comprised in the shelf 56b, however, openings 57 may be comprised in the frame 56a or both the shelves 56b and the frame 56a. Furthermore, the openings 57 may be directed in any suitable direction.

Figure 2B:
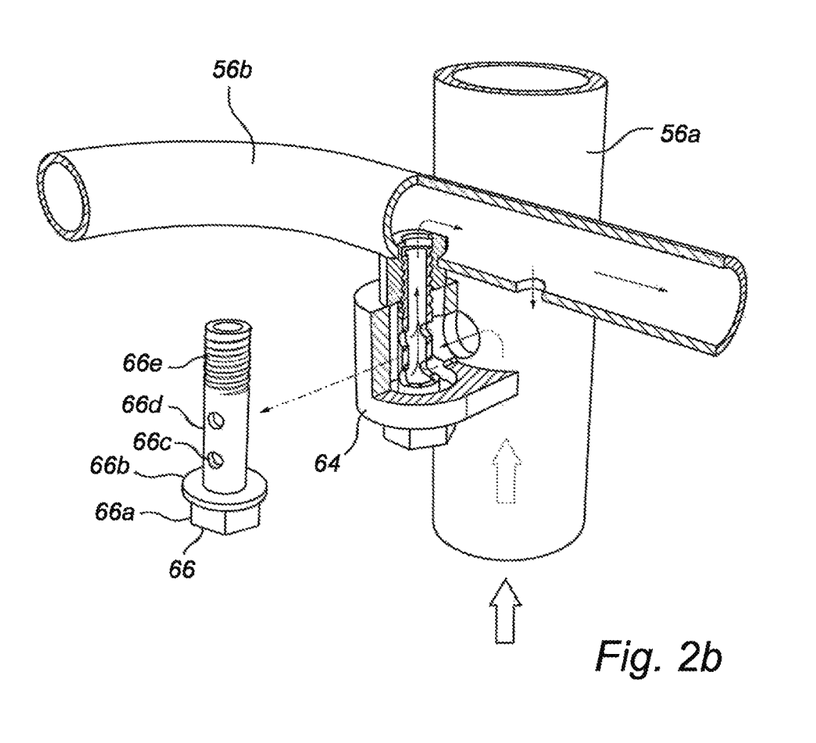

With reference to FIG. 2b, which is a schematic perspective cutaway view of one of the connectors 58, the connector 58 comprises a hollow shelf holder 64 and a hollow fastening screw 66. The flow of fluid is indicated by arrows. The hollow fastening screw 66 comprises a screw head 66a for tightening the shelf holder 64 to the shelf 56b, a screw washer 66b for sealing the hollow shelf holder 64, a screw opening 66c for allowing the flow of fluid from the frame 56a to the hollow shelf holder 64, a screw body 66d, and a screw lead 66e for threading the fastening screw 66 to the shelf 56b. The hollow fastening screw 66 and the hollow shelf holder 64 are arranged such that a clearance is provided between the screw body 66d and the interior of the hollow shelf holder 64. Hereby, the hollow fastening screw 66 may be arranged in any direction while preventing the opening 66c to bear against an interior wall of the hollow shelf holder 64. By the configuration illustrated in FIG. 2b the flow of fluid is allowed to flow from the frame 56a to the shelf 56b via the connector 58.

Figure 3:
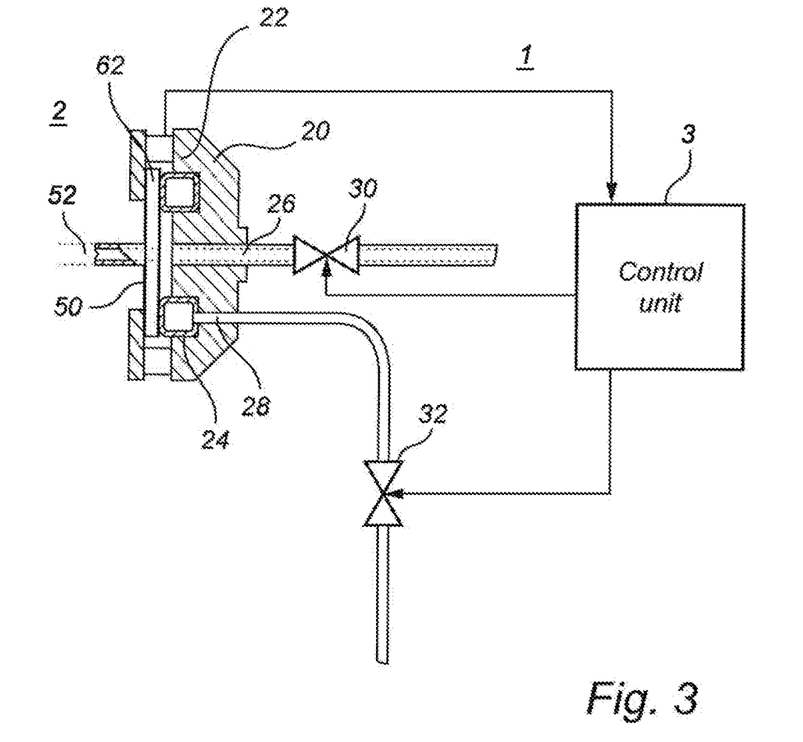
FIG. 3 is a block diagram schematically illustrating the connection between the removable sterilization rack and the sterilization apparatus.

The connection of the docking port 50 of the sterilization rack 2 to the fluid supply port 20 of the sterilization apparatus 1 will now be further described with reference to FIG. 3. As illustrated in FIG. 3, the fluid supply port 20 further comprises a seal 24 for sealing the fluid supply port 20 to the docking port 50, a first fluid supply conduit 26 for supplying fluid to the fluid supply port 20, a second fluid supply conduit 28 for supplying fluid to the seal 24, and a sensor 22 for sensing the marker 62 and thereby detecting when the sterilization rack 2 is arranged inside the sterilization apparatus 1. The marker 62 may be arranged to other parts of the sterilization rack 2 and the sensor 22 may be arranged to other parts of the sterilization apparatus 1. The seal 24 is circumferential arranged at a radial distance from the first fluid supply conduit 26 and is connected to the second fluid supply conduit 28. As illustrated in FIG. 3, the sterilization apparatus 1 further comprises a control unit 3, a first controllable valve 30 connected to the first fluid supply conduit 26 and a second controllable valve 32 connected to the second fluid supply conduit 28.

As illustrated in FIG. 3, the control unit 3 is arranged to communicate with the sensor 22 detecting the marker 62 attached to the docking port 50, when the removable sterilization rack 2 is correctly arranged inside the sterilization apparatus 1, that is when the docking port 50 is aligned with the fluid supply port 20. Subsequently, the control unit 3 communicates with the second controllable valve 32, in order for the controllable valve 32 to open and thereby allowing fluid to flow to the seal 24 whereby the seal is expanded and thereby sealing the fluid supply port 20 and the docking port 50. Subsequently, the control unit 3 communicates with the first controllable valve 30, in order for the controllable valve 20 to open and thereby allowing fluid to flow to the fluid supply port 20 via the first fluid supply conduit 26 further to the docking port 50 and the conduit 52. Hereby, the sterilization apparatus 1 may be in fluid flow contact with the sterilization rack 2.

Figure 4A:
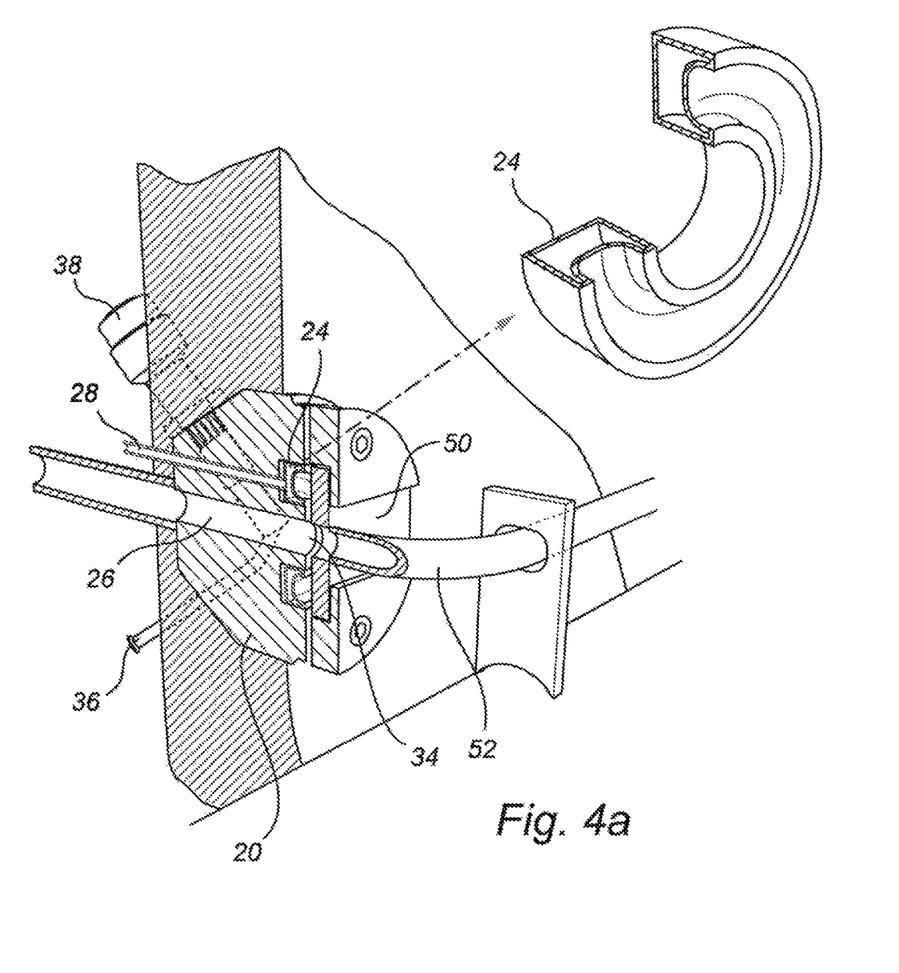
FIG. 4a is a perspective cross sectional view of the connection between the removable sterilization rack and the sterilization apparatus.

The sealing of the docking port 50 to the fluid supply port 20 will now be further described with reference to FIG. 4a and FIG. 4b. In FIG. 4a, the docking port 50 is connected to the fluid supply port 20 and the first fluid supply conduit 26 is arranged to be in (fluid flow) contact with the conduit 52 via a fluid supply outlet 34 of the fluid supply port 20, and the docking port 50. The seal 24 is circumferential arranged at a radial distance from the fluid outlet 26. Furthermore, the seal 24 is connected to the second fluid supply conduit 28, arranged to supply a fluid to the seal 24. In FIG. 4a, no fluid is supplied to the seal 24 and the seal 24 is not in contact with the docking port 50.

As illustrated in FIG. 4a, the fluid supply port 20 further comprises a drain pipe 36 arranged along the fluid supply conduit 26, and a valve 38 arranged along the fluid supply conduit 26 between the drain pipe 36 and the fluid supply outlet 34.

The drain pipe 36 is configured for draining the removable sterilization rack 2. Furthermore, the valve 38 is arranged to close and open the fluid supply conduit 26 to the fluid supply outlet 34. By the arrangement of the drain pipe 36, a fluid path between the fluid supply conduit 26 and the drain pipe 36 is provided when the valve 38 closes the fluid supply conduit 26 to the fluid supply outlet 34. Steam may be provided into the fluid path to remove microbiological growth and other impurities in the fluid supply conduit 26 and the drain pipe 36.

Figure 4B:
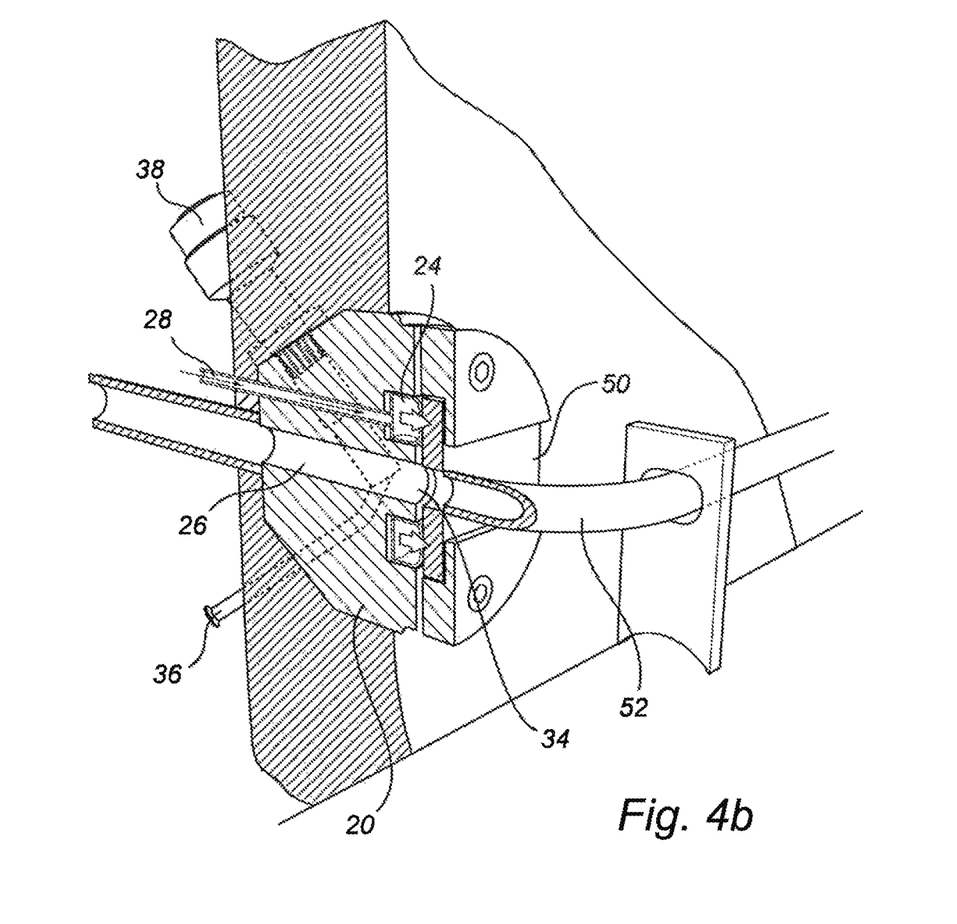
FIG. 4b is a perspective cross sectional view of the connection between the removable sterilization rack and the sterilization apparatus.

In FIG. 4b, the seal 24 is expanded by a fluid, e.g. air, which is being supplied to the seal 24 through the second fluid supply conduit 28. Hereby, the seal comes into contact with the docking port 50, sealingly connecting the fluid supply port 20 to the docking port 50.

Additionally, variations to the disclosed embodiments can be understood and effected by the skilled person in practicing the claimed invention, from a study of the drawings, the disclosure, and the appended claims. For example, the sterilization apparatus and the removable sterilization rack may be configured differently than presented here, while using the same type of connection connecting the sterilizing apparatus to the removable sterilization rack.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A removable sterilization rack for supporting objects to be sterilized inside a sterilization apparatus, the sterilization rack comprising:
    a support structure for supporting the objects, the support structure comprising a frame and at least one shelf releasably attached to the frame using at least one fastener configured to mechanically attach the shelf to the frame and to provide a flow channel between the frame and the at least one shelf;
    at least one opening in the support structure for directing a flow of a fluid towards the objects when the objects are supported by the support structure;
    a docking port for docking with a fluid supply port of the sterilization apparatus and for receiving fluid from the fluid supply port of the sterilization apparatus; and
    a conduit configured to provide a fluid flow path between the docking port and the at least one opening,
    wherein the sterilization rack comprises a marker configured to provide a contactless positioning indication to the sterilization apparatus when the docking port is in a position to receive fluid from the fluid supply port of the sterilization apparatus.

2. The removable sterilization rack according to claim 1, wherein the marker comprises a magnet.

3. The removable sterilization rack according to claim 1, wherein the marker is disposed in the docking port.

4. The removable sterilization rack according to claim 1, wherein the frame is a tubular frame,
    the tubular frame constituting at least a part of the conduit.

5. The removable sterilization rack according to claim 4, wherein the at least one opening is in the tubular frame.

6. The removable sterilization rack according to claim 4, wherein the at least one shelf has a tubular portion in fluid flow connection with the tubular frame, wherein the at least one opening is in the tubular portion.

7. The removable sterilization rack according to claim 6, wherein the fastener comprises a hollow screw to provide a flow channel between the tubular frame and the tubular portion of the at least one shelf.

8. The removable sterilization rack according to claim 1, wherein the frame is a tubular frame and the at least one fastener comprises a hollow screw to provide a flow channel between the tubular frame and a tubular portion of the at least one shelf.

\* \* \* \* \*